(12) United States Patent
Schwab et al.

(10) Patent No.: US 11,458,260 B2
(45) Date of Patent: Oct. 4, 2022

(54) SPRAY CANISTER DEVICE WITH REMOVABLE SLEEVED COVER

(71) Applicant: Bemis Manufacturing Company, Sheboygan Falls, WI (US)

(72) Inventors: Brian Schwab, East Chatham, NY (US); Shao-Yu Peng, Changhua County (TW); Brian Murray, Albany, NY (US)

(73) Assignee: Bemis Manufacturing Company, Sheboygan Falls, WI (US)

( * ) Notice: Subject to any disclaimer, the term of this patent is extended or adjusted under 35 U.S.C. 154(b) by 218 days.

(21) Appl. No.: 15/649,564

(22) Filed: Jul. 13, 2017

(65) Prior Publication Data

US 2018/0015238 A1    Jan. 18, 2018

Related U.S. Application Data

(60) Provisional application No. 62/363,232, filed on Jul. 16, 2016.

(51) Int. Cl.
*A61M 11/00* (2006.01)
*B05B 11/00* (2006.01)
(Continued)

(52) U.S. Cl.
CPC ........... *A61M 11/006* (2014.02); *A61M 11/08* (2013.01); *A61M 35/003* (2013.01);
(Continued)

(58) Field of Classification Search
CPC .. A61M 11/006; A61M 35/003; A61M 11/08; A61M 15/009; A61M 11/007;
(Continued)

(56) References Cited

U.S. PATENT DOCUMENTS

| 2,875,450 A | 3/1959 | Umann |
|---|---|---|
| D198,085 S | 4/1964 | Rich |

(Continued)

FOREIGN PATENT DOCUMENTS

| CN | 201551648 | 8/2010 |
|---|---|---|
| CN | 101933781 | 1/2011 |

(Continued)

OTHER PUBLICATIONS

PCT Notification of Transmittal of The International Search Report and The Written Opinion of The International Searching Authority, or Declaration; PCT/US2017/031485, filed on May 6, 2017 by Whole Bath, LLC.

(Continued)

*Primary Examiner* — Nicholas J. Weiss
*Assistant Examiner* — Alessandro R Del Priore
(74) *Attorney, Agent, or Firm* — Michael Best & Friedrich LLP

(57) ABSTRACT

A method and apparatus is provided for spraying a solution, such as a cleaning solution a barrier material, out of a spray canister device to a surface area of a human body. The spray canister device generally includes a removable sleeved cover element covering an inner canister element. The spray canister device with the removable sleeved cover is easy to carry and easy to spray, and can be handled manually or functions together with other devices.

9 Claims, 6 Drawing Sheets

(51) Int. Cl.

| | | |
|---|---|---|
| *B65D 51/24* | (2006.01) | |
| *B65D 25/34* | (2006.01) | |
| *B65D 41/02* | (2006.01) | |
| *A61M 11/08* | (2006.01) | |
| *B65D 83/14* | (2006.01) | |
| *A61M 35/00* | (2006.01) | |
| *B65D 83/38* | (2006.01) | |
| *E03D 9/08* | (2006.01) | |
| *A47K 5/12* | (2006.01) | |
| *A61M 15/00* | (2006.01) | |
| *B65D 83/26* | (2006.01) | |
| *B05B 15/70* | (2018.01) | |

(52) U.S. Cl.
CPC .......... *B05B 11/3053* (2013.01); *B65D 25/34* (2013.01); *B65D 41/02* (2013.01); *B65D 51/242* (2013.01); *B65D 83/759* (2013.01); *E03D 9/085* (2013.01); *A47K 5/12* (2013.01); *A61M 15/009* (2013.01); *B05B 15/70* (2018.02); *B65D 83/267* (2013.01); *B65D 83/386* (2013.01)

(58) Field of Classification Search
CPC ....... A61M 31/00; A61M 11/00; E03D 9/085; B65D 83/759; B65D 41/02; B65D 25/34; B65D 51/242; B65D 83/267; B65D 83/386; B65D 83/20; B65D 83/201; B65D 83/202; B05B 11/3053; B05B 15/70; B05B 1/02; B05B 1/3026; B05B 7/2421; B05B 11/0027; B05B 11/0032; B05B 11/0038; B05B 11/047; B05B 11/3001; B05B 11/3015; B05B 11/3023; B05B 11/3069; B05B 11/3074; B05B 11/309; B05B 12/085; B05B 12/12; B05B 15/74; B05B 1/34; B05B 11/00412; B05B 11/00418; B05B 11/0089; B05B 11/0091; B05B 11/0097; B05B 11/3014; B05B 11/3022; B05B 11/3047; B05B 11/3052; B05B 11/306; B05B 12/00; B05B 12/006; B05B 12/18; B05B 13/0431; B05B 14/42; B05B 15/18; B05B 15/60; B05B 15/72; B05B 1/00; B05B 1/04; B05B 1/14; B05B 1/304; B05B 1/323; B05B 3/003; B05B 3/005; B05B 3/021; B05B 3/0431; B05B 3/0477; B05B 3/0481; B05B 3/0486; B05B 5/025; B05B 5/0255; B05B 5/04; B05B 5/053; B05B 7/0483; B05B 7/2424; A47K 5/12; B05C 17/005; B05C 17/00; B05C 17/00513; B05C 17/00516; B05C 17/00576; B05C 17/0133; F17C 5/06; B05D 1/02; B05D 2401/20; B05D 2504/00; B05D 2520/00; B05D 3/007; B05D 3/0413; B05D 3/0486; B05D 3/12; B05D 7/14; B05D 7/227; B05D 7/56

See application file for complete search history.

(56) References Cited

U.S. PATENT DOCUMENTS

| | | | |
|---|---|---|---|
| 3,306,252 A * | 2/1967 | Knight .................. | B65D 83/22 |
| | | | 128/200.23 |
| 3,516,424 A * | 6/1970 | Eagle ................. | A46B 11/0017 |
| | | | 132/148 |
| 3,810,260 A | 5/1974 | Lodi | |
| 3,995,326 A | 12/1976 | Umann | |
| 4,067,499 A * | 1/1978 | Cohen .................. | A61M 11/007 |
| | | | 239/323 |
| 4,279,362 A | 7/1981 | Pursell | |
| 4,287,618 A | 9/1981 | Silver | |
| 4,327,560 A | 5/1982 | Leon et al. | |
| D266,758 S | 11/1982 | Johannsen | |
| 4,422,189 A | 12/1983 | Couvrette | |
| 4,428,512 A * | 1/1984 | Nosek .................. | B65D 83/201 |
| | | | 222/402.15 |
| D279,184 S | 6/1985 | Sakamoto | |
| 4,628,548 A | 12/1986 | Kurosawa et al. | |
| D303,966 S | 10/1989 | Fritzsche | |
| 4,903,347 A | 2/1990 | Garcia et al. | |
| 4,987,617 A | 1/1991 | Furukawa et al. | |
| 5,031,252 A | 7/1991 | Oyama | |
| 5,101,520 A | 4/1992 | Lockhart | |
| 5,201,080 A | 4/1993 | Tanaka et al. | |
| 5,203,037 A | 4/1993 | Kang | |
| 5,247,711 A | 9/1993 | Kwon | |
| 5,335,855 A | 8/1994 | Borod | |
| D355,246 S | 2/1995 | Kawamura | |
| 5,409,167 A | 4/1995 | Borod | |
| D367,922 S | 3/1996 | Kobayashi | |
| 5,504,948 A | 4/1996 | Chandler | |
| 5,551,098 A | 9/1996 | Wilk | |
| 5,566,402 A | 10/1996 | Agha el.Rifai et al. | |
| 5,630,234 A | 5/1997 | Childs | |
| D387,851 S | 12/1997 | Pieters | |
| 5,720,054 A | 2/1998 | Nakayama et al. | |
| 5,765,238 A | 6/1998 | Furukawa et al. | |
| 5,813,060 A | 9/1998 | Klopocinski | |
| 5,864,894 A | 2/1999 | Fedele | |
| 5,898,956 A | 5/1999 | Kurisaki et al. | |
| 5,911,516 A | 6/1999 | Chang | |
| 5,941,419 A * | 8/1999 | Molinary ............. | B65D 83/202 |
| | | | 222/83.5 |
| 5,953,765 A | 9/1999 | Hayashi et al. | |
| 5,987,659 A | 11/1999 | Cannizzaro | |
| 6,003,159 A | 12/1999 | Sadegh et al. | |
| 6,009,570 A | 1/2000 | Hargest | |
| D423,655 S | 4/2000 | Otte | |
| 6,073,275 A | 6/2000 | Klopocinski | |
| 6,105,178 A | 8/2000 | Kurisaki et al. | |
| D432,220 S | 10/2000 | Hulsebus | |
| 6,128,788 A | 10/2000 | Yamazaki | |
| D435,638 S | 12/2000 | Merry | |
| 6,167,577 B1 | 1/2001 | Hammad | |
| 6,178,568 B1 | 1/2001 | Boulieris | |
| 6,192,527 B1 | 2/2001 | Paul | |
| D451,076 S | 11/2001 | Sommer et al. | |
| D451,177 S | 11/2001 | Scholpp | |
| 6,339,852 B1 | 1/2002 | Huang | |
| 6,397,406 B1 | 6/2002 | Moshkovich | |
| 6,449,780 B1 | 9/2002 | Merry | |
| 6,481,590 B1 | 11/2002 | Simkins | |
| D471,966 S | 3/2003 | Kazuya | |
| D481,016 S | 10/2003 | Hillis | |
| D485,337 S | 1/2004 | Tani | |
| 6,688,500 B1 | 2/2004 | Cheng | |
| 6,691,328 B2 | 2/2004 | Delfino | |
| 6,754,912 B1 | 6/2004 | Hayashi et al. | |
| D500,130 S | 12/2004 | Jung | |
| D508,733 S | 8/2005 | Peng | |
| D512,425 S | 12/2005 | Satoshi | |
| 6,973,679 B1 | 12/2005 | Schad | |
| 7,096,518 B2 | 8/2006 | Takenaga | |
| D528,991 S | 9/2006 | Katsuyama et al. | |
| 7,120,946 B1 | 10/2006 | Lazar | |
| 7,127,750 B2 | 10/2006 | Lim | |
| D533,788 S | 12/2006 | Kleiman | |
| 7,155,755 B2 | 1/2007 | Olivier | |
| D538,907 S | 3/2007 | Kaule | |
| 7,191,473 B2 | 3/2007 | Matsomoto et al. | |
| D541,225 S | 4/2007 | Katsuyama et al. | |
| 7,216,374 B2 | 5/2007 | Hassan | |
| 7,284,285 B2 | 10/2007 | Scalzi | |
| 7,287,286 B2 | 10/2007 | Lee | |
| D554,613 S | 11/2007 | Takeshi | |
| D558,181 S | 12/2007 | Takada | |
| D564,976 S | 3/2008 | Billings et al. | |
| D565,554 S | 4/2008 | Fan | |

(56) References Cited

U.S. PATENT DOCUMENTS

| | | | |
|---|---|---|---|
| D578,515 S | 10/2008 | Ikeda et al. | |
| D579,342 S | 10/2008 | Priestman | |
| D583,030 S | 12/2008 | Kobayashi | |
| D594,537 S | 6/2009 | Driedger | |
| D594,945 S | 6/2009 | Nakasaki et al. | |
| 7,543,339 B1 | 6/2009 | Harris | |
| D608,426 S | 1/2010 | Hiroaki | |
| D616,445 S | 5/2010 | Wong et al. | |
| D634,735 S | 3/2011 | Maier | |
| D639,399 S | 6/2011 | Takeuchi | |
| D639,400 S | 6/2011 | Kang | |
| 7,954,181 B2 | 6/2011 | Lim | |
| 8,060,953 B1 | 11/2011 | Dorra | |
| D654,808 S | 2/2012 | Gidlow | |
| 8,161,580 B2 | 4/2012 | Hashidume et al. | |
| 8,261,377 B2 | 9/2012 | Oh | |
| D668,642 S | 10/2012 | Feldman et al. | |
| 8,291,527 B2 | 10/2012 | Pan et al. | |
| D670,659 S | 11/2012 | Ishikawa et al. | |
| D671,935 S | 12/2012 | Mao | |
| 8,365,317 B1 | 2/2013 | Dorra | |
| 8,425,475 B2 | 4/2013 | Sodo | |
| D682,246 S | 5/2013 | Boqueho | |
| D688,359 S | 8/2013 | Ogata et al. | |
| D692,417 S | 10/2013 | Tu | |
| D692,541 S | 10/2013 | Hosoi et al. | |
| D698,754 S | 2/2014 | Bertrand | |
| D703,797 S | 4/2014 | Shinozaki | |
| D704,316 S | 5/2014 | Yuji | |
| D704,317 S | 5/2014 | Yoshihiko | |
| D706,402 S | 6/2014 | Yeung | |
| D708,954 S | 7/2014 | Barnes | |
| 8,776,278 B1 | 7/2014 | Dorra | |
| D713,815 S | 9/2014 | Ookawa | |
| D715,774 S | 10/2014 | Lee et al. | |
| D716,768 S | 11/2014 | Ki-Soo | |
| D717,930 S | 11/2014 | Kergoet | |
| 8,904,575 B1 | 12/2014 | Lindheimer et al. | |
| D724,058 S | 3/2015 | Chandel | |
| D724,059 S | 3/2015 | Kim | |
| 9,049,970 B2 | 6/2015 | Dorra | |
| 9,084,864 B1 * | 7/2015 | Schroeder | A61M 16/0816 |
| D750,765 S | 3/2016 | Giametta | |
| 9,273,454 B2 | 3/2016 | Slawinski | |
| 9,279,241 B2 | 3/2016 | Morioka et al. | |
| D753,095 S | 4/2016 | Evangeline | |
| 9,464,425 B2 | 10/2016 | Bailey | |
| D781,808 S | 3/2017 | Pista | |
| D792,867 S | 7/2017 | Patrick | |
| D805,615 S | 12/2017 | Shao-Yu | |
| 9,889,982 B2 | 2/2018 | Falcon | |
| 2001/0004083 A1 * | 6/2001 | Brotspies | B05B 11/3052 |
| | | | 222/162 |
| 2003/0140407 A1 | 7/2003 | Matsumoto et al. | |
| 2004/0055080 A1 | 3/2004 | Marshall | |
| 2005/0000006 A1 | 1/2005 | Takenaga | |
| 2005/0010997 A1 | 1/2005 | Olivier | |
| 2006/0000012 A1 | 1/2006 | Schad | |
| 2006/0265801 A1 | 11/2006 | Riccobon | |
| 2007/0241929 A1 | 10/2007 | Marchetto | |
| 2008/0047055 A1 | 2/2008 | Lim | |
| 2008/0055394 A1 | 3/2008 | Shiue | |
| 2008/0201837 A1 | 8/2008 | Oh | |
| 2008/0251551 A1 | 10/2008 | Huber et al. | |
| 2009/0313752 A1 | 12/2009 | Kunimoto et al. | |
| 2010/0012685 A1 | 1/2010 | Ramsey | |
| 2010/0152475 A1 | 6/2010 | Raichle | |
| 2010/0176224 A1 * | 7/2010 | Hasselschwert | B05B 5/03 |
| | | | 239/708 |
| 2011/0132929 A1 | 6/2011 | Bennett | |
| 2011/0133001 A1 | 6/2011 | Cooper | |
| 2011/0191950 A1 | 8/2011 | Liu | |
| 2011/0203044 A1 | 8/2011 | Lim | |
| 2011/0284601 A1 * | 11/2011 | Pullin | A45C 11/00 |
| | | | 29/463 |
| 2012/0005817 A1 | 1/2012 | Jeong | |
| 2012/0011647 A1 | 1/2012 | Mochita | |
| 2012/0150148 A1 | 6/2012 | Shi | |
| 2012/0180785 A1 | 7/2012 | Trill et al. | |
| 2012/0218106 A1 * | 8/2012 | Zaima | G16H 40/63 |
| | | | 340/540 |
| 2012/0266483 A1 | 10/2012 | Palermo et al. | |
| 2013/0133131 A1 | 5/2013 | Peng | |
| 2013/0180041 A1 | 7/2013 | Ding | |
| 2013/0267890 A1 | 10/2013 | Li | |
| 2014/0042195 A1 | 2/2014 | Geis | |
| 2014/0047626 A1 | 2/2014 | Dorra | |
| 2014/0068862 A1 | 3/2014 | Al-Jafar | |
| 2014/0101838 A1 | 4/2014 | Gupta et al. | |
| 2014/0107409 A1 | 4/2014 | Bailey et al. | |
| 2015/0000025 A1 | 1/2015 | Clements | |
| 2015/0059076 A1 | 3/2015 | Tiagai | |
| 2015/0203279 A1 * | 7/2015 | Falcon | B65D 83/386 |
| | | | 222/402.15 |
| 2015/0225167 A1 | 8/2015 | Anderson et al. | |
| 2015/0337525 A1 | 11/2015 | Bailey | |
| 2016/0316978 A1 | 11/2016 | Peng | |
| 2017/0021116 A1 | 1/2017 | Rahmel | |
| 2017/0142306 A1 | 5/2017 | Peng | |
| 2017/0265624 A1 * | 9/2017 | Wilson | B05B 11/3004 |
| 2017/0319794 A1 | 11/2017 | Schwab | |
| 2017/0321406 A1 | 11/2017 | Schwab | |
| 2017/0321407 A1 | 11/2017 | Schwab | |
| 2017/0321408 A1 | 11/2017 | Schwab | |
| 2018/0028797 A1 | 2/2018 | Schwab | |
| 2018/0036473 A1 | 2/2018 | Schwab | |
| 2018/0044903 A1 | 2/2018 | Schwab | |
| 2019/0186116 A1 | 6/2019 | Schwab | |

FOREIGN PATENT DOCUMENTS

| | | | |
|---|---|---|---|
| DE | 1625201 | 2/1970 | |
| EM | 025022450001 | 7/2014 | |
| EP | 2138640 | 12/2009 | |
| FR | 2671294 | 7/1992 | |
| FR | 2671294 A1 * | 7/1992 | B65D 83/386 |
| FR | 2869596 | 11/2005 | |
| FR | WO 2008/024005 A2 | 2/2008 | |
| GB | 2351779 | 1/2001 | |
| JP | S4815806 | 2/1973 | |
| JP | H0893034 | 4/1996 | |
| JP | H0988165 | 3/1997 | |
| JP | H1163666 | 3/1999 | |
| JP | 2001279778 | 10/2001 | |
| JP | 2003286738 | 10/2003 | |
| JP | 2003342993 | 12/2003 | |
| JP | 2007321443 | 12/2007 | |
| JP | 2015206183 | 11/2015 | |
| KR | 2012/044086 A2 | 4/2017 | |
| TW | 469317 | 12/2001 | |
| WO | 2013020240 | 2/2013 | |

OTHER PUBLICATIONS

PCT Notification of Transmittal of The International Search Report and The Written Opinion of The International Searching Authority, or Declaration, PCT/US2017/031482, filed on May 6, 2017 by Whole Bath, LLC.

PCT Notification of Transmittal of The International Search Report and The Written Opinion of The International Searching Authority, or Declaration, PCT/US2017/031483, filed on May 6, 2017 by Whole Bath, LLC.

Kohler, Self-Cleaning Wand, https://www.youtube.com/watch?v=z629hpdnWj8, published Oct. 12, 2016.

Final Office Action for U.S. Appl. No. 15/588,640 dated Dec. 3, 2018.

PCT Notification of Transmittal of The International Search Report and The Written Opinion of the International Searching Authority, PCT/2017/031484, dated Aug. 14, 2017.

PCT Notification of Transmittal of The International Search Report and The Written Opinion of The International Searching Authority, PCT/US2016/45932, dated Oct. 24, 2016.

(56) References Cited

OTHER PUBLICATIONS

PCT Notification of Transmittal of The International Search Report and The Written Opinion of The International Searching Authority, PCT/US2017/042288, dated Sep. 28, 2017.
Schwabcare website 2017, http://schwabcare.com/, site visited Jan. 21, 2018.
PCT Notification of Transmittal of The International Search Report and The Written Opinion of The International Searching Authority, or Declaration; PCT/US2017/42253, filed on Jul. 14, 2017 by Whole Bath, LLC.
PCT Notification of Transmittal of The International Search Report and The Written Opinion of The International Searching Authority, or Declaration; PCT/US2017/031484, filed on May 6, 2017 by Whole Bath, LLC.
Office Action from Chinese Patent Application No. 2017800570280, with English translation, dated Nov. 27, 2019; 22 pages.
Extended Euorpean Search Report for European Application No. 17831614 dated Mar. 18, 2020.
Extended European Search Report for European Patent Application No. 17831608.9 dated Feb. 25, 2020.

\* cited by examiner

SPRAY CANISTER DEVICE WITH REMOVABLE SLEEVED COVER

CROSS-REFERENCE TO RELATED APPLICATIONS

This application claims benefit of U.S. provisional patent application Ser. No. 62/363,232, filed Jul. 16, 2016, which is herein incorporated by reference.

BACKGROUND OF THE INVENTION

Embodiments of the present invention generally relate to a spray device and particularly to a spray canister device for the delivery of water, medication, solutions and/or a pharmaceutical formulation to a surface area of a human subject. More specifically, aspects of the present invention provide a method and device for delivering and applying water, medication, and/or a cleaning solution to a region of a human body (e.g., skin, genital or anal area, intimate parts, perianal region).

DESCRIPTION OF THE RELATED ART

People who have problems controlling their urine or bowels and suffer from incontinence are at risk of skin problems around the buttocks, hips, genitals, and the area between the pelvis and rectum (perineum). Excess moisture in these areas may result in skin problems (e.g., redness, peeling, irritation, and yeast infections, etc.), and if the person spends most of his or her day in a wheelchair, or bed, it is likely that bedsores may also develop. Such skin problem may be worse if the person uses diapers and other products, which allow urine or stool to be in constant contact with the skin. As such, special care by cleaning and drying the area right away after urinating or having a bowel movement, and/or cleaning the skin with mild, dilute soap and water then rinsing well and gently patting dry.

In addition, moisturizing creams can help keep the skin moist. Also, a skin sealant or moisture barrier, barrier creams or ointments that contain occlusive, barrier-type topical, such as zinc oxide, lanolin, or petrolatum can form a protective barrier on the skin. Some skin care products, often in the form of a spray or a towelette, create a clear, protective film over the skin. A doctor or nurse can recommend barrier creams to help protect the skin. There are a wide variety of ointments, creams, barrier sprays, or lotions known and available in the market for the treatment of diaper rash or incontinence. Most of these products include ingredients that offer some beneficial property to the product, for example, by acting as a skin protectant, water repellant, emollient, neutralizer or antibiotic.

In applying skin protection paste, ointments, barrier sprays, lotions, solutions, and fluids to an individual's skin. If the individual is alone, this is impossible since an individual cannot adequately apply skin protection fluid onto hard-to-reach areas of his or her own back and bottom. Accordingly, it is necessary to utilize the services of a second individual to apply the skin protection fluid on hard-to-reach areas such as the back and upper neck. Thus, there is a need for an easy-to-grip and easy-to-handle spray device for applying fluids, solutions, suspensions, or paste to the skin area of a person.

SUMMARY OF THE INVENTION

The present invention generally provides a method and small-scale apparatus that is easy to grip and easy to handle for the delivery of water, medication, cleaning solutions, moisturizing creams, skin sealant, moisture barrier, medicaments, and/or a pharmaceutical formulation to a surface area of a human subject. In one embodiment, a spray canister device is provided and includes a sleeved cover element and an inner canister element. In one aspect, the sleeved cover element is removable to be separated from the inner canister element.

In one embodiment, the sleeved cover element includes a top cap portion, an opening, a sleeve portion, a handle grip, and a trigger bar. In another embodiment, the inner canister element includes a top outlet and a canister body. In one aspect, the canister body of the inner canister element is covered by the sleeved portion of the removable sleeved cover element and the top outlet is fitted to channels inside the top cap portion of the removable sleeved cover element.

In still another embodiment, the canister element further includes a ring portion and a bottom portion. In one aspect, the interior content of the canister element is sprayed out by triggering the trigger bar of the sleeved cover element against the canister element and moving the bottom portion of the canister element to be closer to the opening of the sleeved cover element.

Still further, the sleeved cover element further includes a top flat surface portion. In one aspect, the interior content of the canister element is sprayed out by pushing down the top flat surface portion of the sleeved cover element.

Embodiments of the invention further provide a method for easy gripping and easy handling of the spray canister device. The method includes positioning a spray canister device, which includes a sleeved cover element, an opening on the sleeved cover element, and a canister element, near a surface area of a human subject, moving the sleeved cover element against the canister element of the spray canister device, and spraying out droplets of a solution from the spray canister device. The method may further include shaking the spray canister device prior to being used.

In one aspect, droplets of a solution are sprayed out from the spray canister device by pushing the bottom portion of the spray canister device against one or more trigger bars on a sleeved cover element of the spray canister device. In another aspect, droplets of a solution are sprayed out from the spray canister device by pushing down a top flat surface portion of the sleeved cover element and spraying out droplets of the solution from the spray canister device.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the present invention include a method and an apparatus for providing easy application of skin protection paste, ointments, barrier sprays, lotions, solutions, and fluids to an individual's skin. For maximum protection it is necessary to apply the skin protection fluid/solution or barrier materials over the entire exposed surface area of the individual's skin by using a spraying mechanism. If the individual is alone, this is impossible since an individual cannot adequately apply skin protection fluid onto hard-to-reach areas of his or her own back and bottom. The invention provides a canister spray device to be applied for a person to apply on his or her own or with the services of a second individual to apply and spray the skin protection fluid/solution on hard-to-reach areas such as the back, the bottom, and/or upper neck of the person. The spray canister device contains a handle grip which allows for the benefits of easy-to-grip, easy to carry, and easy to hang, among others. The spray canister device as described herein is easy-to-handle and easy to apply and spray fluids, solutions, suspensions, or paste of a barrier chemical or medicament to the skin area of a person.

Figure 1:
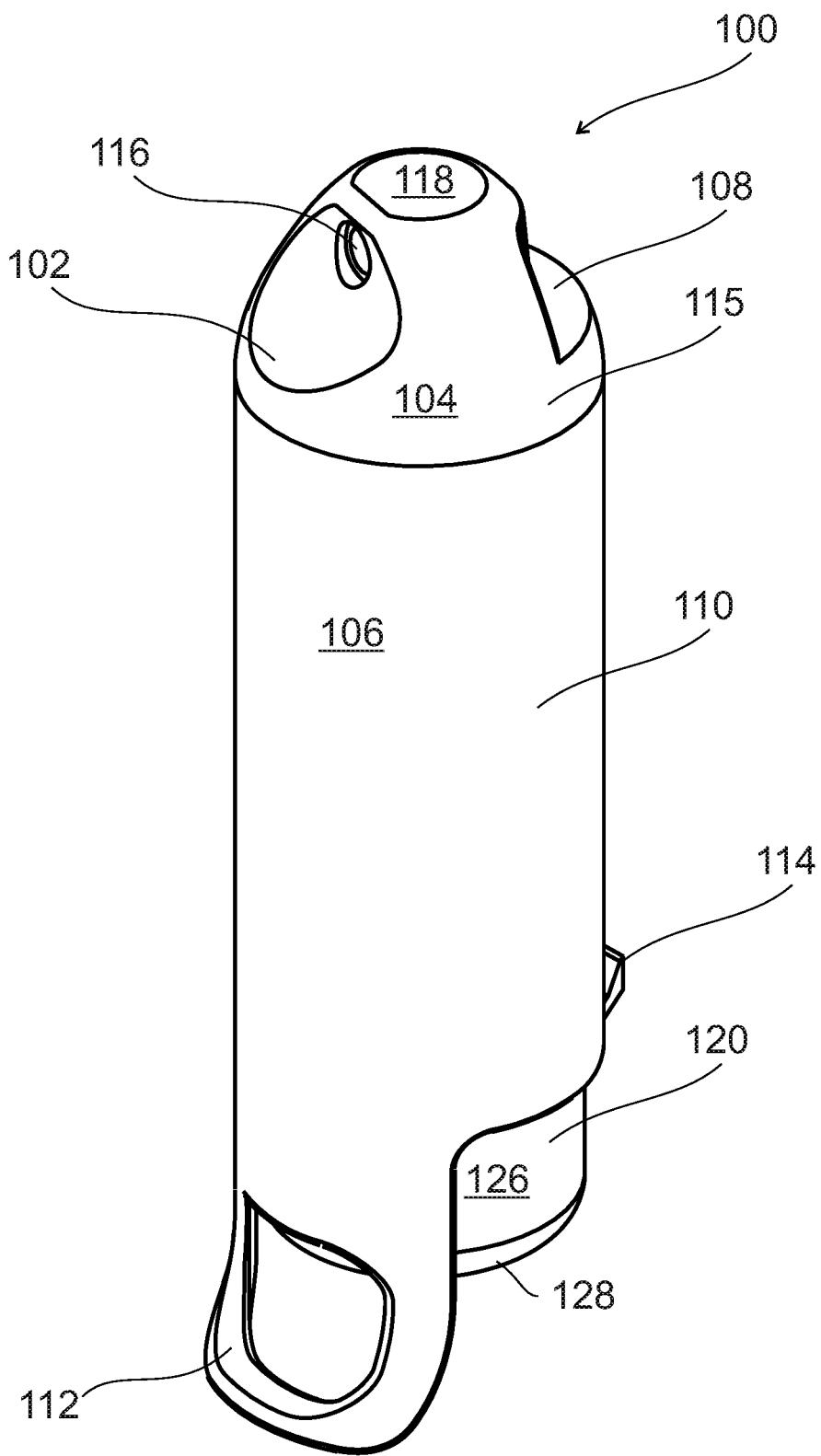
FIG. 1 is a perspective view of a spray canister device according to one embodiment of the invention.
Figure 4:
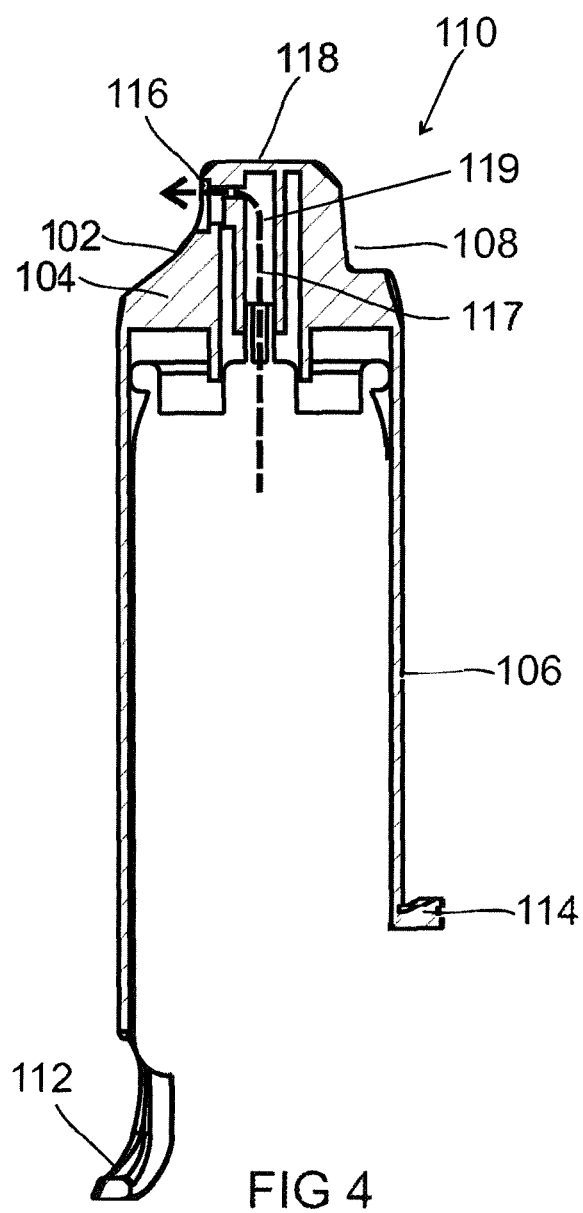
FIG. 4 is a cross-sectional view of a removable sleeved cover element of a spray canister device according to another embodiment of the invention.
Figure 5:
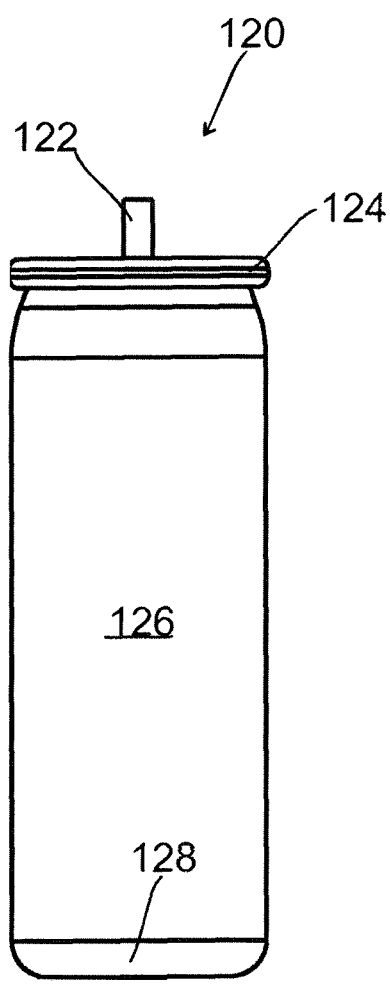
FIG. 5 is a side view of an inner canister element of a spray canister device according to still another embodiment of the invention.

The spray canister device with the removable sleeved cover element is easy to carry and easy to spray, and can be handled manually or functions together with other devices. FIG. 1 illustrates one example of a spray canister device 100 according to one embodiment of the invention. The spray canister device 100 includes a sleeved cover element 110 and a canister element 120. In one aspect, the sleeved cover element 110 is removable to be separated from the canister element 120 (as shown in FIG. 4 and FIG. 5). In another aspect, the canister element 120 can be removable positioned in and out of an inner wall portion of the sleeved cover element 110. In still another aspect, the sleeved cover element 110 surrounds a portion of the canister element (as shown in FIG. 1), or alternatively, the sleeved cover element 110 covers the whole body of the canister element 120.

As shown in FIG. 1, the sleeved cover element 110 includes a top cap portion 104 and a sleeve portion 106. The top cap portion 104 may include a top body portion 108 and a cut-out portion 102. The top cap portion 104 may include a ring portion 115 forming the base of the top cap portion 104 so that the shape of the ring portion 115 conforms to the shape of the sleeve portion 106. In one aspect, the cut-out portion 102 includes one or more openings 116 for spraying out droplets or mist of a cleaning solution or a medicated solution or ointment stored inside the canister element 120.

For example, the canister element 120 can be used to store a cleaning solution or a medicated solution to a surface area of a human body to be sprayed out by the opening 116 of the sleeved cover element of the spray canister device 100 so that it is easy to operate and use. Examples of ingredients that are commonly included inside the inner canister element of the spray canister device 100 are ointment, paste or solutions of mineral oil, silicone fluids (e.g. dimethicone and cyclomethicone), petrolatum, cod liver oil, lanolin, zinc oxide, talc, calamine, kaolin, topical starch and allantoin. For example, Desitin® ointment (Pfizer, Inc.) is probably the most common topical used in treating diaper rash and other rashes. It contains common barrier materials (zinc oxide and petrolatum) and additionally contains two common skin conditioning agents (cod liver oil and lanolin).

Figure 2A:
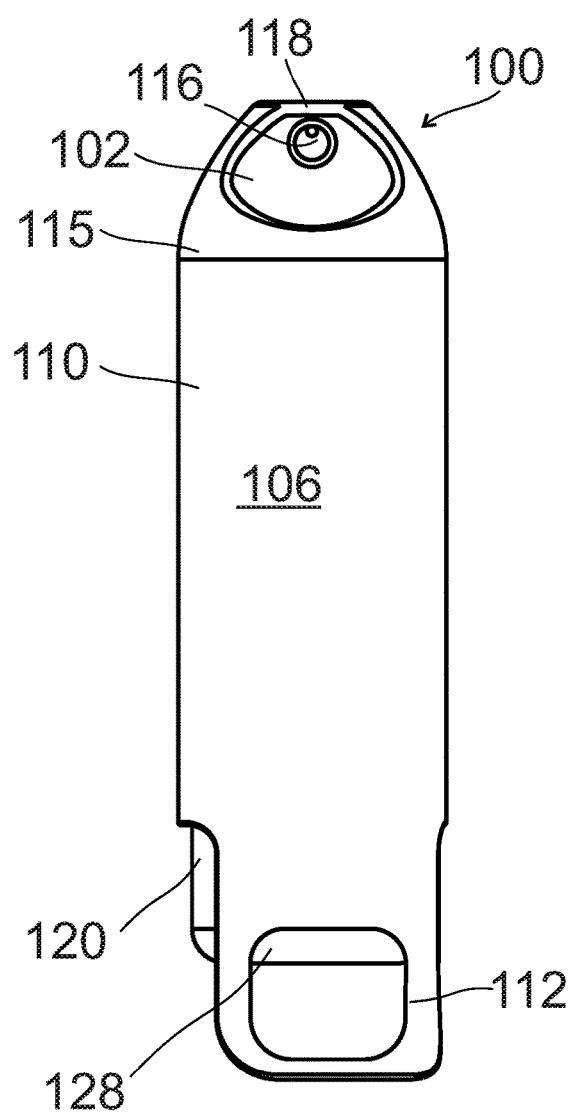
FIG. 2A is a front view of a spray canister device according to another embodiment of the invention.
Figure 2B:
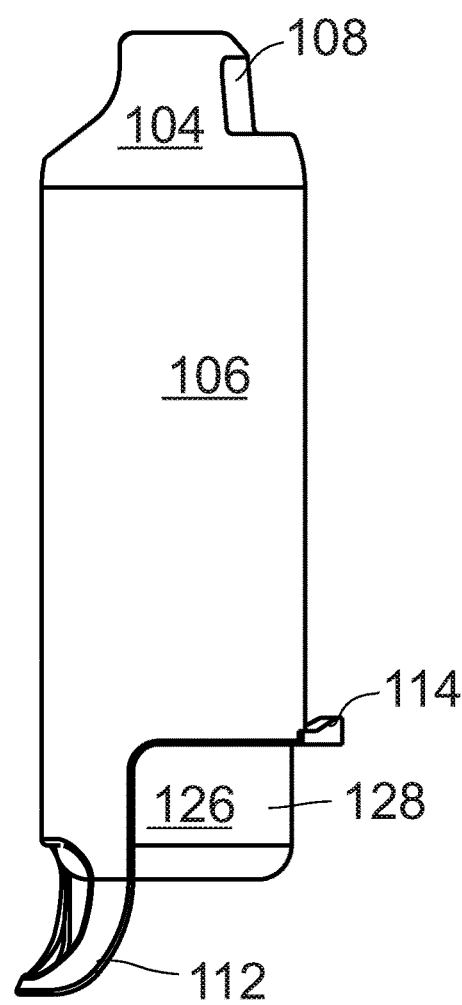
FIG. 2B is side view of a spray canister device according to another embodiment of the invention.

FIG. 2A is a front view of the spray canister device 100 and FIG. 2B is side view of the spray canister device 100, showing that the sleeved cover element 110 covering and surrounding the canister element 120 to form into the spray canister device 100. As shown in FIGS. 2A and 2B, the sleeved cover element 110 includes a handle grip 112, and a trigger bar 114. In addition, the canister element 120 may include a canister body 126 and a bottom portion 128.

The handle grip 112 of the sleeved cover element 110 is used for easy-to-grip, easy to carry, and easy to hang the whole device, among others, and the trigger bar 114 of the sleeved cover element 110 is used to assist in spraying the content inside the canister body 120 such that the spray canister device 100 as described herein is easy-to-handle and easy to apply and spray fluids, solutions, suspensions, or paste of a barrier chemical or medicament to the skin area of a person.

Figure 3A:
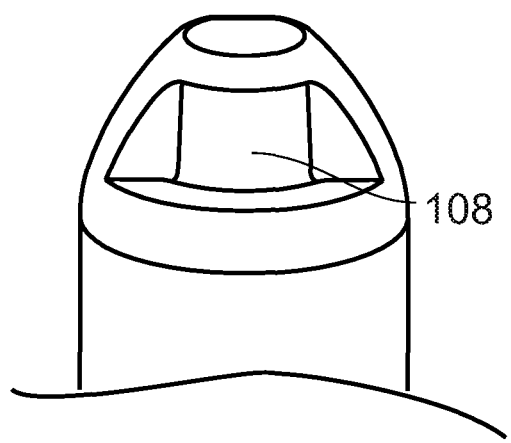
FIG. 3A is a side view of a top portion of a spray canister device according to another embodiment of the invention.
Figure 3B:
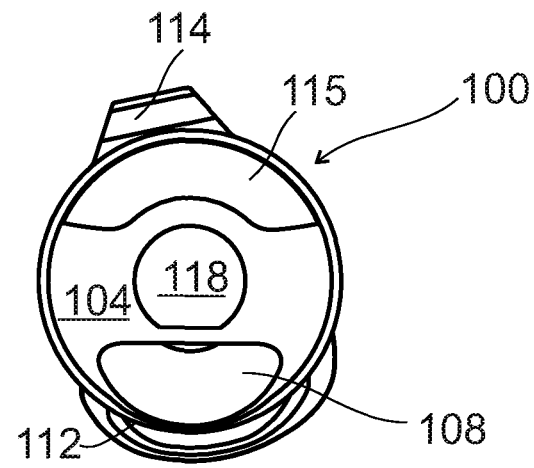
FIG. 3B is a top view of a spray canister device according to one embodiment of the invention.

FIG. 3A is a side view of a top portion of the spray canister device 100 and FIG. 3B is a top view of the spray canister device 100. The sleeved cover element 110 of the spray canister device 100 may further include the top body portion 108 with channels 117 therein and a top flat surface portion 118 for easy handling. In one aspect, the interior content of the canister element 120 is sprayed out by pushing down the top flat surface portion 118 of the sleeved cover element 110 to atomize the content of the cleaning or medicated solution inside the canister element 120 and spray out droplets or mists of the barrier materials, medicaments or cleaning solutions.

FIG. 4 is a cross-sectional view of only the sleeved cover element 110 being removed and separated from the canister element 120. As shown in FIG. 4, one or more channels 117 inside the top cap portion of the sleeved cover element 110 are used to deliver a cleaning or medicated solution inside the canister element 120 and spray droplets or mists of the barrier materials, medicaments or cleaning solutions out of the opening 116. As illustrated, the channel 117 is formed as a conduit 119 having an angled flow path (e.g., a 90-degree turn) between the outlet 122 of the canister element 120 and the opening 116.

FIG. 5 is a side view of only the canister element 120 without any covering by the sleeved cover element 110. In FIG. 5, the inner canister element 120 includes include a top outlet 122, a ring portion 124, the canister body 126, and the bottom portion 128. In one aspect, the canister body 126 of the canister element 120 is covered by the sleeved portion 106 of the sleeved cover element 110 and the top outlet 122 is fitted to channels 117 inside the top cap portion of the removable sleeved cover element.

Figure 6:
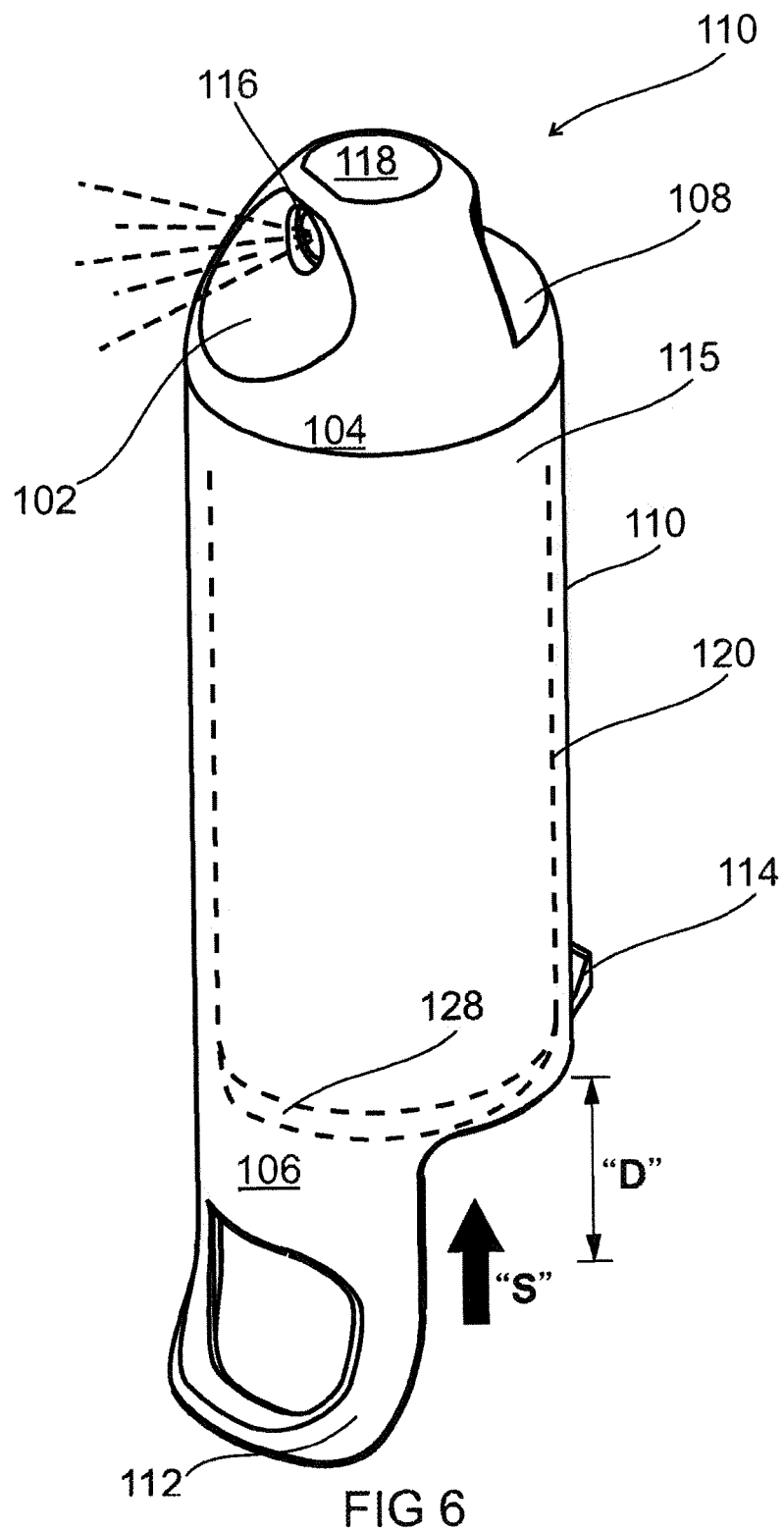
FIG. 6 is a perspective view of operating a spray canister device according to yet another embodiment of the invention.

FIG. 6 is a perspective view of operating a spray canister device according to one embodiment of the invention. In one aspect, the spray canister device is operated by pushing the trigger bar 114 of the sleeved cover element 110 against the canister element 120 and moving the bottom portion 128 of the canister element in the direction "S" so as to be closer in distance to the opening 116 of the sleeved cover element 110. As such, the interior content of the canister element 120 is sprayed out of the spray canister device 100 via the opening 116.

Figure 7:
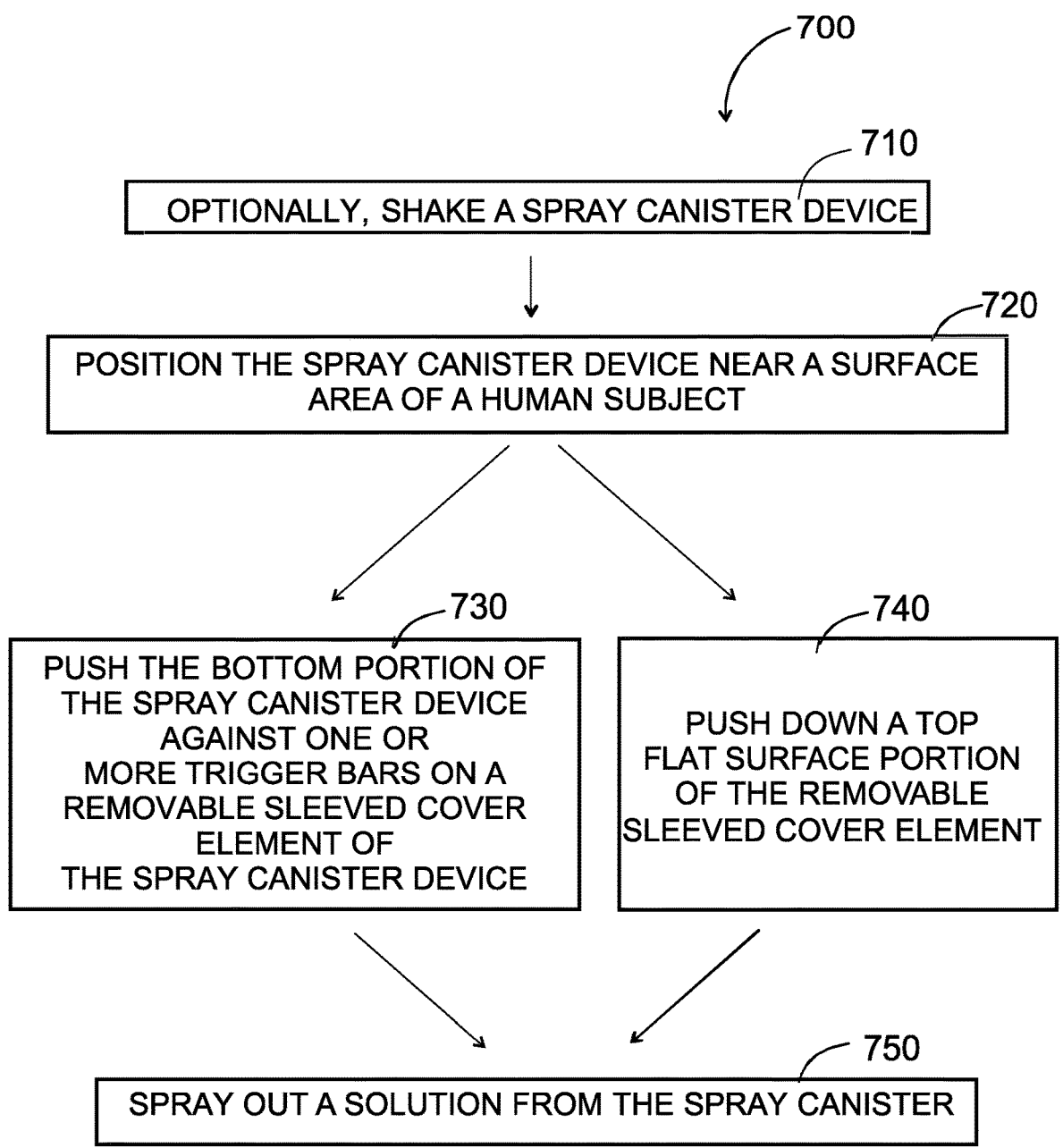
FIG. 7 illustrates a method of operating a spray canister device according to another embodiment of the invention.

FIG. 7 illustrates one example of a method 700 of operating the spray canister device 100 according to one or more embodiments of the invention. As shown in FIG. 7, the method 700 includes one or more steps 710, 720, 730, 740 and 750. Optionally, at step 710 of a spray canister device is shaken prior to being used to apply a spray near or onto a skin area of a subject, such as a human subject.

At step 720, the spray canister device is positioned near a surface area of the subject. The spray canister device includes a sleeved cover element, an opening on the sleeved cover element, and a canister element. One example of the spray canister device is the spray canister device 100 as described herein.

At step 730, the sleeved cover element is moved against the canister element of the spray canister device. In one aspect, a human subject operates the spray canister device by pushing the bottom portion of the canister element of the spray canister device against one or more trigger bars on a sleeved cover element of the spray canister device.

In an alternate aspect, at step 740, a human subject operates the spray canister device by pushing down a top flat surface portion of the sleeved cover element.

Finally, at step 750, a barrier material or medicated solution or any other suitable solution stored at the canister element of the spray canister device is sprayed out of the spray canister device into droplets of the solution.

In one embodiment, the spray canister device 100 may further includes a power switch such that various motors and electric circuits can be used to turn on or powering up the spray canister device 100.

Accordingly, a method and a spray canister device that is easy to carry and operate are provided for applying a barrier, protectant or medicated solution to protect, clean or cure a skin area of a human body.

While the foregoing is directed to embodiments of the present invention, other and further embodiments of the invention may be devised without departing from the basic scope thereof, and the scope thereof is determined by the claims that follow.

The invention claimed is:

1. A spray canister device, comprising:
a sleeved cover element comprising a top flat surface closing a top portion of the cover element, a sleeve portion, a cap portion extending from a first end of the sleeve portion, and a handle grip extending from a second end of the sleeve portion opposite the first end thereof, the cap portion having an opening on a side of the cap portion; and
a canister element comprising a bottom portion and an outlet, wherein the canister element is configured for containing a liquid product therein, the liquid product comprising one or more of a barrier material, a medicament, and a cleaning solution;
wherein the canister element is positioned within the sleeve portion of the sleeved cover element such that the outlet of the canister element is in fluid communication with the opening of the cap portion via a channel;
wherein the handle grip of the sleeved cover element includes an aperture therethrough, the handle grip extending beyond the bottom portion of the canister element when the canister element is positioned in the sleeve portion;
wherein the bottom portion is configured to be moveable towards the opening of the cap portion such that relative motion of the canister element and the sleeved cover element towards one another causes release of the liquid product from the outlet of the canister element through the channel and out of the opening of the cap;
wherein the sleeved cover element further includes a trigger bar to facilitate relative movement between the sleeved cover element and the canister element to compress the outlet of the canister element and dispense said liquid product; and
wherein the trigger bar is positioned on a side of the second end of the sleeve portion opposite the handle grip.

2. The spray canister device of claim 1, wherein the channel is formed as an angled conduit providing an angled path extending from the outlet of the canister element away from the bottom portion of the canister and curving upstream of the top flat surface to reach the opening on the side of the cap portion, for flow of the liquid product after the liquid product exits the outlet of the canister element.

3. The spray canister device of claim 1, wherein the canister element is removable from the sleeved cover element.

4. The spray canister device of claim 1, wherein the cap portion of the sleeved cover element includes a manually depressible portion permitting dispensing of said liquid product upon depression of same.

5. The spray canister device of claim 1, wherein the bottom portion of the canister element extends beyond the second end of the sleeve portion.

6. The spray canister device of claim 1, wherein the bottom portion of the canister element does not extend beyond the second end of the sleeve portion.

7. The spray canister device of claim 1, wherein the trigger bar is wedge-shaped.

8. The spray canister device of claim 1, wherein at least a portion of the handle grip is flared outward in a radial direction relative to a longitudinal axis of the sleeve portion.

9. The spray canister device of claim 1, wherein the sleeved cover element is monolithic.

* * * * *